US007883890B2

(12) United States Patent
Kawakami et al.

(10) Patent No.: US 7,883,890 B2
(45) Date of Patent: Feb. 8, 2011

(54) TRANSPOSON TRANSFER FACTOR FUNCTIONED IN MAMMAL

(75) Inventors: Koichi Kawakami, Chiba (JP); Tetsuo Noda, Miyagi (JP)

(73) Assignee: Research Organization of Information and Systems, Tokyo (JP)

( * ) Notice: Subject to any disclaimer, the term of this patent is extended or adjusted under 35 U.S.C. 154(b) by 818 days.

(21) Appl. No.: 10/504,535

(22) PCT Filed: Feb. 14, 2003

(86) PCT No.: PCT/JP03/01569

§ 371 (c)(1),
(2), (4) Date: Mar. 25, 2005

(87) PCT Pub. No.: WO03/068960

PCT Pub. Date: Aug. 21, 2003

(65) Prior Publication Data

US 2005/0177890 A1    Aug. 11, 2005

(30) Foreign Application Priority Data

Feb. 15, 2002    (JP)    ............................. 2002-038971

(51) Int. Cl.
*C12N 5/0735* (2010.01)
(52) U.S. Cl. .................... 435/354; 435/320.1; 435/463; 514/44
(58) Field of Classification Search .................. None
See application file for complete search history.

(56) References Cited

U.S. PATENT DOCUMENTS 6,492,575 B1    12/2002    Wagner et al.
7,034,115 B1 *    4/2006    Kawakami .................. 530/350

FOREIGN PATENT DOCUMENTS

| JP | 2000-516463 | 12/2000 |
| WO | WO 01/30965 | 5/2001 |
| WO | WO 01/40477 | 6/2001 |

OTHER PUBLICATIONS

Kawakami et al., Gene, 1998, vol. 225, pp. 17-22.*
Luo et al., Proc. Natl. Acad. Sci. USA, vol. 95, pp. 10769-10773, Sep. 1998.*
Esposito, T., et al., "A novel pseudoautosomal human gene encodes a putative protein similar to Ac-like transposases," *Hum. Mol. Genet.* 8:61-67, Oxford University Press (1999).
Koga, A., et al., "The medaka fish *Tol2* transposable element can undergo excision in human and mouse cells," *J. Hum. Genet.* 48:231-235, Springer-Verlag (published online Mar. 2003).
Koga, A., et al., "Gene Transfer and Cloning of Flanking Chromosomal Regions Using the Medaka Fish *Tol2* Transposable Element," *Mar. Biotechnol.* 4:6-11, Springer-Verlag New York Inc. (Jan. 2002).
Koga, A., et al., "Transposable Elements in Medaka Fish," *Zoological Sci.* 19:1-6, Zoological Society of Japan (Jan. 2002).

Supplementary European Search Report for European Application No. EP 03 70 5172, European Patent Office, Netherlands, mailed Oct. 6, 2005.
Sekikawa, K., "Purpose and Meaning of Production of Transgenic Animals," *Norin Suisan Giyjutsu Kenkyu Journal* 23:6-8, Maruzen Co Ltd (2000).
English Translation of Sekikawa, K., "Purpose and Meaning of Production of Transgenic Animals," *Norin Suisan Gijyutsu Kenkyu Journal* 23:6-8, Maruzen Co Ltd (2000) (Document NPL15).
Takahashi, S., et al., "Cloning Technology and Transgenic Animals," *Norin Suisan Gijyutsu Kenkyu Journal* 23:9-14, Maruzen Co Ltd (2000).
English Translation of Takahashi, S., et al., "Cloning Technology and Transgenic Animals," *Norin Suisan Gijyutsu Kenkyu Journal* 23:9-14, Maruzen Co Ltd (2000) (Document NPL17).
Wakayma, T., et al., "Mice cloned from embryonic stem cells," *Proc. Natl. Acad. Sci. U.S.A.* 96:14984-14989, National Academy of Sciences (1999).
Fischer, S.E.J., et al., "Regulated transposition of a fish transposon in the mouse germ line," *Proc. Natl. Acad. Sci. USA* 98:6759-6764, National Academy of Sciences (Jun. 2001).
Kawakami, K., and Noda, T., "Transposition of the *Tol2* Element, an *Ac*-Like Element From the Japanese Medaka Fish *Oryzias latipes*, in Mouse Embryonic Stem Cells," *Genetics* 166:895-899, Genetics Society of America (Feb. 2004).
Kawakami, K., and Shima, A., "Identification of the *Tol2* transposase of the medaka fish *Oryzias latipes* that catalyzes excision of a nonautonomous *Tol2* element in zebrafish *Danio rerio*," *Gene* 240:239-244, Elsevier Science (1999).
Koga, A., et al., "Transposable element in fish," *Nature* 383:30, MacMillan Magazines Ltd. (1996).
Koga, A., et al., "Amino acid sequence of a putative transposase protein of the medaka fish transposable element *Tol2* deduced from mRNA nucleotide sequences," *FEBS Lett.* 461:295-298, Elsevier Science (1999).
Zagoraiou, L., et al., "In vivo transposition of *Minos*, a *Drosophila* mobile element, in mammalian tissues," *Proc. Natl. Acad. Sci. USA* 98:11474-11478, National Academy of Sciences (Sep. 2001).
Fischer, S.E.J., et al., "Regulated transposition of a fish transposon in the mouse germ line," *Proc. Natl. Acad. Sci. USA* 98:6759-6764, National Academy of Sciences (Jun. 2001).
Kawakami, K., and Noda, T., "Transposition of the Tol2 Element, an Ac-Like Element From the Japanese Medaka Fish *Oryzias latipes*, in Mouse Embryonic Stem Cells," *Genetics* 166:895-899, Genetics Society of America (Feb. 2004).
Kawakami, K., and Shima, A., "Identification of the Tol2 transposase of the medaka fish *Oryzias latipes* that catalyzes excision of a nonautonomous Tol2 element in zebrafish *Danio rerio*," *Gene* 240:239-244, Elsevier Science (1999).
Koga, A., et al., "Transposable element in fish," *Nature* 383:30, MacMillan Magazines Ltd. (1996).

(Continued)

*Primary Examiner*—James S Ketter
(74) *Attorney, Agent, or Firm*—Sterne, Kessler, Goldstein & Fox P.L.L.C.

(57) ABSTRACT

Genetically modified mammalian cells comprising a Tol2 transposon transferred into a chromosome can be obtained by co-transfecting mammalian cells with a Tol2 transposase encoded by a Tol2 transposon found in medaka fish, and a Tol2 transposon lacking this transposase.

13 Claims, 2 Drawing Sheets

OTHER PUBLICATIONS

Koga, A., et al., "Amino acid sequence of a putative transposase protein of the medaka fish transposable element Tol2 deduced from mRNA nucleotide sequences," *FEBS Lett.* 461:295-298, Elsevier Science (1999).

Zagoraiou, L., et al., "In vivo transposition of Minos, a *Drosophila* mobile element, in mammalian tissues," *Proc. Natl. Acad. Sci. USA* 98:11474-11478, National Academy of Sciences (Sep. 2001).

NCBI Entrez, GenBank Report, Accession No. AB031079, entry date Mar. 1, 2002.

NCBI Entrez, GenBank Report, Accession No. AB033244, entry date Mar. 28, 2002.

NCBI Entrez, GenBank Report, Accession No. D84375, entry date Feb. 27, 2002.

* cited by examiner

FIG. 2a
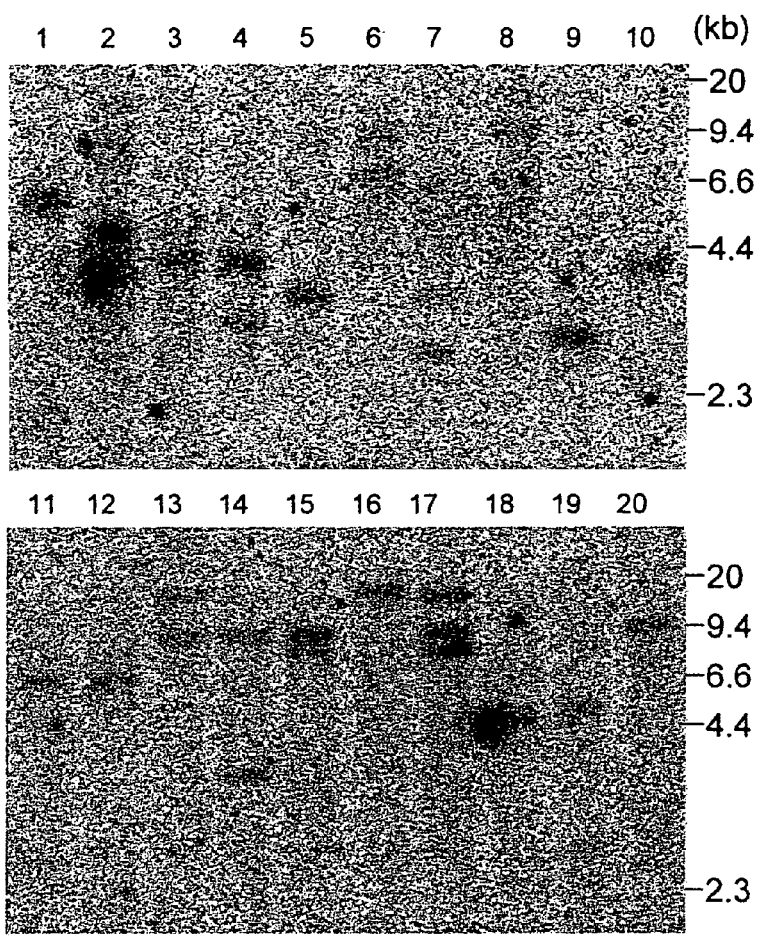
FIG. 2b
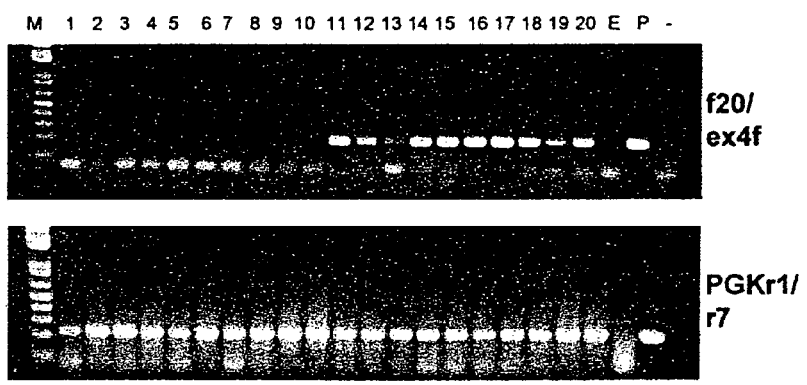
FIG. 2c
1 TGGGAATTAT<u>GACAGTAGC</u>AG-*Tol2*-*CT*GGACAGTAGTAGCTTGATT
9 AGAAAAATCT<u>CTGCCATT</u>*CAG*-*Tol2*-*CT*GCTGCCATTCCAACAGTCT
10 GCGACAGGGAGGGCTGCACAG-*Tol2*-*CT*GGGGCTGCAGAGTGGTGGG

TRANSPOSON TRANSFER FACTOR FUNCTIONED IN MAMMAL

TECHNICAL FIELD

The present invention relates to transposases capable of inducing transposition in mammals, transposons retaining these transposases, nonautonomous transposons that can be transposed in mammals, and methods for producing genetically modified animals using these transposases, and the like.

BACKGROUND ART

Transposons are a powerful tool in molecular biology and genetic research. They are broadly used in bacteria, plants, and invertebrates for mutagenesis, preparation of transgenic individuals, and such. On the other hand, the development of such techniques in vertebrates has been slow. In recent years, a synthetic transposon system called "Sleeping Beauty" has been constructed by connecting Tc1-like transposon fragments, which were discovered in salmonid fish (Ivics, Z., Hackett, P. B., Plasterk, R. H., & Izsvak, Z. Cell 91, 501-510 (1997)). The transposition of this transposon has also been confirmed in mouse embryonic stem cells and germ cell lines, etc. (Luo, G., Ivics, Z., Izsvak, Z. & Bradley, A. Proc. Natl. Acad. Sci. USA 95, 10769-10773 (1998); Yant, S. R., Meuse, L., Chiu, W., Ivics, Z., Izsvak, Z. & Kay, M. A. Nat. Genet. 25: 35-41 (2000); Fischer, S. E., Wienholds, E. & Plasterk, R. H. Proc. Natl. Acad. Sci. USA 98: 6759-6764 (2001); Horie. K., Kuroiwa, A., Ikawa, M., Okabe, M., Kondoh, G., Matsuda, Y. & Takeda, J. Proc. Natl. Acad. Sci. USA 98, 9191-9196 (2001); Dupuy, A. J. Fritz, S. & Largaespada, D. A. Genesis 30: 82-88 (2001)).

While "Sleeping Beauty" is a synthetic transposon, an active natural transposon has also been discovered in vertebrates. This transposon, Tol2, is the only natural transposon in vertebrates, and was cloned from the medaka fish (killifish) genome (Koga, A., Suzuki, M., Inagaki, H., Bessho, Y., & Hori, H. Nature 383, 30 (1996)). Since the Tol2 sequence is analogous to that of the Ac element in maize, it has been classified into the hAT family of transposons. Furthermore, the transposition of this Tol2 has not only been observed in medaka fish embryos (Koga, A., & Hori, H. Genetics 156, 1243-1247 (2000)), but also in the germ line of zebrafish (Kawakami, K., Koga, A., Hori, H., & Shima, A. Gene 225, 17-22 (1998); Kawakami, K., & Shima, A. Gene 240, 239-244 (1999); Kawakami, K., Shima, A., & Kawakami, N. Proc. Natl. Acad. Sci. USA 97, 11403-11408 (2000)). However, it has not been found in mammals.

Such transposons are expected to become extremely useful in both forward genetics, wherein genetic analysis is based on the phenotype of mammalian cells after mutagenesis, and reverse genetics, wherein phenotype analysis is based on genes introduced during preparation of transgenic individuals and such.

DISCLOSURE OF THE INVENTION

In order to discover functional transposons that will be powerful tools in the gene analysis of mammals, a primary objective of the present invention is to analyze the activity of Tol2 in mammalian cells. Another objective is to develop the likes of methods for genetic modification in mammals using this Tol2 transposon.

To achieve the above objectives, the present inventors investigated whether Tol2 transposon is transposable in mammals, and as a result, discovered that Tol2 transposon also functions in mammals. In particular, chromosomal transposition of Tol2 transposon could be detected by incorporating a Tol2 transposase encoded by the Tol2 transposon, and a Tol2 transposon lacking this transposase into different vectors, and cotransfecting animals. Based on these findings, the present inventors developed the invention described below.

(1) A DNA encoding a transposase comprising the activity of inducing transposition within mammalian cells, comprising the nucleotide sequence of SEQ ID NO: 1.

(2) A DNA encoding a transposase comprising the activity of inducing transposition within mammalian cells, wherein said transposase DNA is a DNA according to the following (A) or (B):
  (A) a DNA encoding a protein comprising an amino acid sequence in which one or more amino acids are substituted, deleted, inserted, and/or added to the amino acid sequence of SEQ ID NO: 2, or
  (B) a DNA hybridizing under stringent conditions with a DNA comprising the nucleotide sequence of SEQ ID NO: 1.

(3) A DNA complementary to a DNA comprising the nucleotide sequence of SEQ ID NO: 1 or a complementary strand thereof, comprising a length of at least 15 nucleotides.

(4) A transposase encoded by the DNA of (1) or (2).

(5) An RNA encoding the transposase of (4).

(6) A vector comprising the DNA of (1) or (2).

(7) A host cell comprising the DNA of (1) or (2), or the vector of (6).

(8) A DNA transposable in mammalian cells, wherein said DNA is a transposon DNA according to the following (A) or (B):
  (A) a DNA comprising the nucleotide sequence of SEQ ID NO: 3, or
  (B) a DNA hybridizing under stringent conditions with a DNA comprising the nucleotide sequence of SEQ ID NO: 3.

(9) A vector comprising the DNA of (8).

(10) A host cell comprising the DNA of (8) or the vector according to (9).

(11) A DNA complementary to a DNA comprising the nucleotide sequence of SEQ ID NO: 3 or a complementary strand thereof, comprising a length of at least 15 nucleotides.

(12) A DNA nonautonomously transposable in mammalian cells, wherein said DNA is a nonautonomous transposon DNA comprising a deletion, insertion, or substitution of a nucleotide sequence in a transposase-coding region of the nucleotide sequence of SEQ ID NO: 3.

(13) A vector comprising the nonautonomous transposon DNA of (12).

(14) A host cell comprising the nonautonomous transposon DNA of (12) or the vector of (13).

(15) A kit for genetically modifying mammals, comprising the DNA of (8) or the vector of (9).

(16) A kit for genetically modifying mammals, comprising: the nonautonomous transposon DNA of (12) or the vector of (13); and at least one of the transposase DNA of (1) or (2), the vector of (6), the transposase of (4), and the RNA of (5).

(17) The kit for genetically modifying mammals of (16), wherein a site to which a nucleic acid can be inserted is provided in the nonautonomous transposon DNA of (12), or in the region of the nonautonomous transposon DNA of (12) on the vector of (13).

(18) A method for producing genetically modified mammalian cells, comprising the step of introducing the DNA of (8) or the vector of (9) into mammalian cells.
(19) A method for producing genetically modified mammalian cells, comprising the step of introducing mammalian cells with the nonautonomous transposon DNA of (12) or the vector of (13); and at least one of the transposase DNA of (1) or (2), the vector of (6), the transposase of (4), and the RNA of (5).
(20) The method for producing genetically modified mammalian cells of (19), wherein a nucleic acid has been inserted in the nonautonomous transposon DNA of (12) and the region of the nonautonomous transposon DNA of (12) on the vector of (13).
(21) A method for producing genetically modified mammals, comprising the step of injecting the DNA of (8) or the vector of (9) into nonhuman mammals.
(22) A method for producing genetically modified mammals, comprising the step of introducing nonhuman mammals with the nonautonomous transposon DNA of (12) or the vector of (13); and at least one of the transposase DNA of (1) or (2), the vector of (6), the transposase of (4), and the RNA of (5).
(23) A method for producing genetically modified mammals, comprising the step generating individuals by mating a nonhuman mammal comprising the transposase DNA of (1) or (2) with a nonhuman mammal comprising the nonautonomous transposon DNA of (12).
(24) A mammal for producing genetically modified nonhuman mammals, comprising the transposase DNA of (1) or (2) or the nonautonomous transposon DNA of (12).
(25) The method for producing genetically modified mammals of (22), wherein a nucleic acid has been inserted in to the nonautonomous transposon DNA of (12), and the region of the nonautonomous transposon DNA of (12) in the vector according to (13).

Hereinafter, the present invention will be described in detail based on embodiments.

[Autonomous Transposons]

The present invention relates to Tol2 transposon DNA that can be transposed in mammals. In general, the transposition of a transposon requires an enzyme that induces transposition (a transposase) and mobile DNA sequences recognized by this transposase (transposon cis elements). The Tol2 transposons of the present invention are DNA-transposons comprising both. These Tol2 transposons are herein referred to as autonomous Tol2 transposons because they can express transposases and transpose themselves.

Specifically, a typical example of an autonomous Tol2 transposon DNA of this invention is the nucleotide sequence of SEQ ID NO: 3, however, Tol2 transposon DNAs also includes DNAs that are analogous to the Tol2 transposon and can be transposed in mammals in the same way. Examples of such analogous transposon DNAs include DNAs that hybridize under stringent conditions with DNAs comprising the nucleotide sequence of SEQ ID NO: 3.

Stringent hybridization conditions for isolating these DNAs that are functionally equivalent to the Tol2 transposon can be appropriately selected by those skilled in the art. In one example, after prehybridization at 42° C. overnight in a hybridization solution containing 25% formamide (50% formamide under more stringent conditions), 4×SSC, 50 mM Hepes pH 7.0, 10× Denhardt's solution, and 20 ìg/ml denatured salmon sperm DNA, a labeled probe is added, and hybridization is performed by incubation at 42° C. overnight. Subsequent washings can be performed under washing solution and temperature conditions such as "1×SSC, 0.1% SDS, 37° C."; more stringent conditions such as "0.5×SSC, 0.1% SDS, 42° C.", and even more stringent conditions such as "0.2×SSC, 0.1% SDS, 65° C.". More stringent hybridization washing conditions result in the isolation of DNAs that are more homologous to the probe sequence. The aforementioned combinations of SSC and SDS concentrations and temperature conditions are mere examples, and those skilled in the art can determine a stringency similar to that described above by appropriately combining the above-described or other factors that specify hybridization stringency (such as probe concentration, probe length, and hybridization reaction time).

The Tol2 transposon discovered in medaka fish can be obtained from the medaka genomic DNA, but can be easily produced from transformants that comprise the Tol2 transposon, as described below. Furthermore, Tol2 transposon analogues can be obtained by artificially modifying the DNA sequence of SEQ ID NO: 3, or by the above-described hybridization with DNA from species other than medaka fish.

Thus, since the Tol2 transposon and its analogues are autonomously transposable in mammals (mammalian cells), they are useful as tools for mutagenesis, such as the random knockout of genes.

When used as a tool for mutagenesis and such, the Tol2 transposon DNA can be carried by vectors. Vectors can be selected according to the type of host cell, and such selection can be easily conducted by those skilled in the art. For example, vectors for introduction into mammalian cells may be viral vectors, nonviral vectors, or vectors that cannot replicate in mammalian cells. Vectors comprising the Tol2 transposon do not need to autonomously replicate within mammalian cells, so long as the Tol2 transposase encoded by Tol2 transposon can be expressed, and the Tol2 transposon is transposable. Therefore, nonviral vectors may be used where viral vector insertion into cells is undesirable, or an arbitrary DNA sequence or chemical modification that can avoid degradation of the Tol2 transposon DNA may be added.

In addition, the present invention includes not only the full-length Tol2 transposon sequence, but also partial fragments thereof. Such partial fragments are useful as hybridization probes, PCR primers, and such, in analyzing the loci to which a transposon transposes after mutagenesis in mammals. Specifically, such partial fragments are preferably complementary to the DNA comprising the nucleotide sequence of SEQ ID NO: 3, or to its complementary strand, and are long enough to retain specificity as probes, primers, and such, for example, 15 or more nucleotides long.

[Transposases]

The autonomous Tol2 transposon can itself be autonomously transposed within mammals. However, the transposition of Tol2 transposon can also be performed by supplying Tol2 transposase to nonautonomous Tol2 transposons, which are transposase-deficient and unable to autonomously transpose.

The present invention relates to those transposases capable of inducing the transposition of Tol2 transposon in mammals. These transposases are exemplified by, but not limited to, Tol2 transposases that comprise the amino acid sequence of SEQ ID NO: 2. For example, these transposases also include proteins comprising amino acid sequences analogous to the amino acid sequence of SEQ ID NO: 2, and an activity similar to that of Tol2 transposase in mammals. These analogous proteins include proteins comprising transposase activity and an amino acid sequence in which one or more amino acids are substituted, deleted, inserted, and/or added to the amino acid sequence of SEQ ID NO: 2; proteins analogous to a Tol2 transposase from another organism; and artificially produced Tol2 transposase mutants.

The number and position of amino acid mutations in the term "amino acid sequences in which one or more amino acids are substituted, deleted, inserted, and/or added" is not limited, so long as they are within a range in which the transposition-inducing activity in Tol2 transposase is retained. The number of amino acid mutations is typically thought to be 10% or less of the total amino acids, preferably 5% or less, and more preferably 1% or less.

Although Tol2 transposase can be prepared using medaka fish, it can be easily produced using a transformant that comprises a vector that comprises a DNA encoding Tol2 transposase, as described below.

Furthermore, the above-described proteins, which are analogous to the Tol2 transposase protein, can be prepared using hybridization techniques known to those skilled in the art. For example, proteins analogous to the Tol2 transposase protein can be obtained by 1) using a DNA nucleotide sequence that encodes Tol2 transposase, e.g., the nucleotide sequence of SEQ ID NO: 1 or a part thereof, as a probe to isolate DNAs highly homologous to the Tol2 transposase cDNA from fish such as medaka fish, mammals including humans, and other various species, and 2) preparing proteins from the DNAs thus isolated. Stringent hybridization conditions for isolating such DNAs, which encode polypeptides functionally equivalent to Tol2 transposase, can be appropriately selected by those skilled in the art. In one example, prehybridization is carried out at 42° C. overnight, in a hybridization solution containing 25% formamide (50% formamide under more stringent conditions), 4×SSC, 50 mM Hepes pH 7.0, 10× Denhardt's solution, and 20 ig/ml denatured salmon sperm DNA. A labeled probe is then added, and hybridization is carried out by warming the reaction mixture at 42° C. overnight. Subsequent washings can be performed under solution and temperature conditions such as "1×SSC, 0.1% SDS, 37° C."; more stringent conditions such as "0.5× SSC, 0.1% SDS, 42° C."; or even more stringent conditions such as "0.2×SSC, 0.1% SDS, 65° C.". The more stringent the hybridization washing conditions become, the greater the homology of the isolated DNA to the probe sequence. However, the above-described combinations of SSC and SDS concentrations and temperature condition are mere examples, and those skilled in the art can determine stringencies similar to those described above by appropriately combining the aforementioned or other factors (such as probe concentration, probe length, and hybridization reaction time), which specify hybridization stringency.

Furthermore, it is also possible to prepare proteins analogous to Tol2 transposase by isolating DNAs analogous to the Tol2 transposase DNA using PCR (polymerase chain reaction), which is known to those skilled in the art, using the nucleotide sequence of SEQ ID NO: 1 or portions thereof as primers, and then preparing proteins from the analogous DNAs thus isolated.

In addition, the above-described proteins analogous to Tol2 transposase are not limited to natural proteins, and can be prepared by artificially modifying the Tol2 transposase protein comprising the amino acid sequence of SEQ ID NO: 2. This artificial modification can be performed by site-directed mutagenesis of a DNA encoding the Tol2 transposase protein, for example, the DNA of SEQ ID NO: 1, using techniques known to those skilled in the art, such as the deletion-mutant preparation method, PCR method, and cassette mutation method.

Whether the obtained proteins, which are analogous to the Tol2 transposase, comprise a transposition-inducing activity similar to that of Tol2 transposase, can be assessed by analysis. This analysis can be performed according to the Example described below.

[Transposase DNAs]

DNAs encoding transposases of the present invention (hereinafter referred to as "transposase DNAs") include cDNAs, genomic DNAs, and synthetic DNAs, so long as they are DNAs that encode the activity of inducing transposition.

A preferred example of a cDNA that encodes a transposase of this invention is a cDNA that encodes the above-described Tol2 transposase, specifically, a DNA of SEQ ID NO: 1. In addition to this cDNA, cDNAs comprising an activity similar to that of Tol2 transposase are also included. Such cDNAs can be screened from cDNA libraries derived from biological tissues in which proteins comprising the aforementioned activity are expressed. Screening can be carried out by labeling DNAs of SEQ ID NO: 1, their fragments, or the like, and using these as probes for hybridization. Alternatively, the above-described cDNAs may be prepared by RT-PCR by using synthetic oligonucleotides that comprise portions of a DNA of SEQ ID NO: 1 as primers, and with an RNA template derived from tissues expressing proteins that comprise an aforementioned activity.

A preferred example of a genomic DNA that encodes a transposase of the present invention is a DNA of SEQ ID NO: 3. Since this genomic DNA has been identified in medaka fish, it can be obtained from the total DNA of medaka fish, its genomic DNA library, animal genomes such as that of zebrafish into which the transposon has been already introduced, or the like. Furthermore, in addition to the genomic DNAs of SEQ ID NO: 3, genomic DNAs comprising an activity similar to that of Tol2 transposase are also included. Such genomic DNAs may be obtained in the same way as in the above-described preparation of cDNAs, using labeled DNAs of SEQ ID NO: 1 or 3, their fragments, or the like, as probes, and carrying out hybridization from genomic DNA libraries derived from biological tissues. Alternatively, they may be prepared by RT-PCR using synthetic oligonucleotides comprising a portion of a DNA of SEQ ID NO: 1 or 3 as primers, and with a template of RNA derived from biological tissue.

Furthermore, the aforementioned cDNAs and genomic DNAs can also be synthesized using a commercially available DNA synthesizer. For example, they can be prepared by synthesizing a DNA of SEQ ID NO: 1 or 3 and its complementary strand, and then annealing these to form a double strand.

Since the above-described transposase DNAs encode transposases that comprise the activity of inducing transposition within mammalian cells, these DNAs are not only useful as materials for producing these transposases, but can also be used to introduce transposase DNAs directly into mammals, to express the transposases within cells.

The present invention relates to vectors comprising the transposase DNAs. In order to produce the transposases and express them within mammals using the transposase DNAs, as described above, the aforementioned transposase DNAs are preferably incorporated into desired expression vectors. Vectors that can be used herein are not particularly limited, and can be appropriately selected from expression vectors known to those skilled in the art, according to the host in to which a vector comprising a transposase DNA is to be introduced, its usage, and the like. Examples of vectors for expressing transposases in mammals (mammalian cells) include viral vectors such as retroviral vectors, adenoviral vectors, adeno-associated viral vectors, vaccinia viral vectors, lentiviral vectors, herpes viral vectors, alphaviral vectors, EB viral vectors, papilloma viral vectors, and foamy viral vectors; and nonviral vectors such as cationic liposomes, ligand DNA complexes, and gene guns (Y. Niitsu et al. Molecular Medicine 35: 1385-1395 (1998)).

The present invention also includes partial fragments of the transposase DNAs. The above transposase DNAs can be used as total sequences to express the transposases and such, and their partial fragments are also useful as hybridization probes, PCR primers, or ribozyme derivatives. Therefore, for these purposes, these partial fragments are preferably long enough to maintain specificity as a probe, and such. For example, these fragments can be 15 nucleotides or longer. Examples of such polynucleotides are those that specifically hybridize with DNAs comprising the nucleotide sequence of SEQ ID NO: 1 or 3, or complementary strands thereof. Herein, "specifically hybridizing" means that no significant cross hybridization occurs with DNAs that encode other proteins. The above-described probes and primers can be used in cloning DNAs encoding the present protein, and in detecting the present DNAs.

Nucleic acids capable of expressing the transposases of the present invention include not only the above-described DNAs, but also RNAs. RNAs mediate transposase expression from the transposase DNAs. Therefore, transposases can also be expressed within mammalian cells by introducing mammalian cells with transposase RNAs instead of DNAs. Such RNAs can be prepared by transcribing the above-described transposase cDNAs or genomic DNAs, or by using an RNA synthesizer to synthesize RNAs that correspond to the above-described transposase cDNAs.

[Nonautonomous Tol2 Transposons]

Another embodiment of the present invention relates to nonautonomous Tol2 transposons, which are not autonomously transposable in mammals since they lack transposase, and which are transposable on supply of Tol2 transposase.

Tol2 transposons are autonomously transposable. Therefore, after a Tol2 transposon transfers into a mammalian chromosome, it may be excised and transfer to another region. Although such autonomous transposons can act alone to introduce mutations into mammalian chromosomes, they are unstable in terms of the possibility of transposition from a transferred position to another position. Therefore, by deleting the transposase from the Tol2 transposon, the ability to autonomously transfer is deleted, and re-transfer after transfer to a chromosome can be suppressed. Thus, mutations can be stably introduced into chromosomes, and genes can be modified. Such nonautonomous Tol2 transposons include DNAs which have lost their transposase activity due to deletion, insertion, or substitution of a nucleotide sequence in a region encoding the transposase of the above-described transposon DNAs, which comprise the nucleotide sequence of SEQ ID NO: 3, or analogous DNAs comprising equivalent functions.

This deletion, insertion, or substitution of a nucleotide sequence in to a region encoding a transposase is not limited as to the number or type of nucleotides and such in the varied region, so long as it is a mutation that enables loss of transposase activity. It is not limited to mutations in regions encoding a transposase, and also includes mutations that can inhibit transposase expression by a mutation such as deletion, insertion, and substitution in a non-coding region. However, these mutations are limited to those whereby cis elements for transposition are not deficient, to ensure the ability to transfer as a transposon. Such cis elements for transposition can be identified by preparing a series in which the nucleotide sequence of SEQ ID NO: 3 is systematically deleted, using methods known to those skilled in the art, commercially available deletion kits, or the like, and then analyzing regions necessary for transfer.

One example of a deletion mutation in a transposase coding region is that comprising a deletion from 5' side of exon 2 to around the center of exon 4 in Tol2 transposon DNA, as shown in FIG. 1 (specifically, nucleotide 2230 to nucleotide 4146 in SEQ ID NO: 3), but a deletion longer or shorter than this may be used, and the deleted region may be divided into a number of sections. One example of an insertion mutation is a mutation that deletes transposase activity by inserting a linker sequence, restriction enzyme recognition sequence, multicloning site, or arbitrary gene into a transposase-encoding region of the Tol2 transposon, or the like. One example of a substitution mutation is that in which a nucleotide sequence in a transposase-encoding region or the like is substituted with another nucleotide sequence, deleting the transposase's transposition-inducing activity. These deletion, insertion, and substitution mutations may be used singly or in combination. One example of such a combination of mutations is nonautonomous transposon DNA comprising the nucleotide sequence of SEQ ID NO: 4. This DNA comprises a deletion of nucleotides 2230 to 4146 in the Tol2 transposon DNA of SEQ ID NO: 3, and the insertion into this deleted region of a linker sequence comprising a XhoI recognition sequence comprising "AGATCTCATATGCTCGAGGGCCC" (SEQ ID NO: 7).

Such nonautonomous Tol2 transposon DNAs do not themselves comprise transposase activity. Therefore, when introducing a mutation into a chromosome using such DNAs, the DNAs can be stably maintained on the chromosome unless a transposase is supplied from outside. Such mutation introduction is therefore advantageous in identifying functional genes and producing stable transgenic individuals.

Further, the present invention relates to vectors comprising the above-mentioned nonautonomous Tol2 transposon DNAs. While nonautonomous Tol2 transposon DNAs can be used as they are, they can also be connected to vectors, for example, to prevent end portion degradation when introduced into a mammal or mammalian cell. These vectors can be selected depending on the host to be used or their purpose. For example, vectors for introducing these DNAs into mammals (or their cells) can be any of the virus-based vectors (e.g., adenovirus vectors, adeno-associated virus vectors, vaccinia virus vectors, lentivirus vectors, herpes virus vectors, alpha virus vectors, EB virus vectors, papilloma virus vectors, foamy virus vectors, and retrovirus vectors) and nonviral vectors (e.g., cationic liposomes, ligand DNA complexes, and gene guns) (Y. Niitsu et al., Molecular Medicine 35: 1385-1395 (1998)).

Further, the present invention relates to mammalian cells comprising the above-mentioned nonautonomous Tol2 transposon DNAs or vectors comprising the same. Since the nonautonomous Tol2 transposon DNAs in these mammalian cells can transfer and introduce mutations on supply of transposase, such cells comprising the DNAs or vectors can be used to analyze functional genes, manufacture knockout animals, and the like. The host mammalian cells for analysis of functional genes are not particularly restricted, and may be cells derived from primates such as humans, or from rodents such as mice. These mammalian cells may be somatic cells or reproductive cells, and the somatic cells include cells derived from various organs. In the production of knockout animals, cells comprising a reproductive ability, such as germ cells, are preferable for use as the host mammalian cells. In such cells, the above-mentioned DNA or vector may be maintained outside of a chromosome or inside of a chromosome.

[Systems for Producing Mutant Mammalian Cells]

Another embodiment of the present invention relates to systems for modifying mammalian genes. These systems for modifying mammalian genes are systems of modifying mammalian chromosomes using the above-mentioned autonomous or nonautonomous Tol2 transposons. Such "modifications" include knockdown mutations that break existing genes on chromosomes, transgenic mutations that insert novel genes, and modifications including combinations of both.

The first example of a knockdown mutation is a system comprising the above-mentioned autonomous Tol2 transposon DNA, as typified by the nucleotide sequence of SEQ ID NO: 3, or a vector comprising this DNA. As described above, autonomous Tol2 transposon DNAs maintain a transposase and can transfer autonomously in mammalian cells. Therefore, the above-mentioned DNAs or vectors can be introduced into mammalian cells for random gene knockdowns and the like.

A second knockdown mutation system is a system for modifying a mammalian gene that comprises a nonautonomous Tol2 transposon DNA, such as the nucleotide sequence of SEQ ID NO: 4 or a vector comprising this, and at least one of the Tol2 transposase DNAs typified by the nucleotide sequence of SEQ ID NO: 1, a vector comprising this DNA, a transposase as typified by the amino acid sequence of SEQ ID NO: 2, and a RNA encoding this transposase. That is, nonautonomous Tol2 transposon DNAs themselves are not transposable since they lack transposase. However, by supplying mammals with transposase DNAs or RNAs, or directly supplying transposase proteins together with these nonautonomous Tol2 transposon DNAs, the Tol2 transposase DNAs can transfer to chromosomes in the mammals to introduce mutations into random genes on the chromosomes. When a DNA is used as a source for supplying Tol2 transposase, this transposase DNA may be carried by entities other than those carrying the nonautonomous Tol2 transposon DNAs, i.e., separate fragments or separate vectors, or both DNAs may be on the same vector.

A system for transgenic mutation can be the second knockdown mutation system, mentioned above. Namely, a system comprising nonautonomous Tol2 transposon DNAs or vectors comprising such DNAs, and a Tol2 transposase supply source (e.g., DNAs, RNAs, proteins, etc.). For easy use of such systems as systems for transgenic mutation, the above-mentioned nonautonomous transposon DNAs or the nonautonomous transposon DNA regions on the vectors comprising these DNAs preferably comprise a site into which an arbitrary nucleic acid can be inserted. Herein, "an arbitrary nucleic acid" is a nucleic acid whose insertion into a mammalian chromosome is desired, and, for example, genes whose function is to be analyzed can be arbitrarily selected. To facilitate this incorporation of arbitrary nucleic acids into nonautonomous transposon DNAs, a restriction enzyme recognition sequence can be provided as "a site into which an arbitrary nucleic acid can be inserted". Such restriction enzyme recognition sequences may be recognition sites for one restriction enzyme, and may preferably be a multicloning site that comprises recognition sites for a plurality of restriction enzymes. By providing such cloning sites as described above, genes for analysis can be easily inserted into nonautonomous transposon DNAs. By introducing a mammalian cell with a nonautonomous transposon DNA that comprises an arbitrary nucleic acid, along with a Tol2 transposase supplying source (a Tol2 transposase DNA, a vector comprising this, a Tol2 transposase RNA, or a Tol2 transposase protein, transfer of the nonautonomous Tol2 transposon DNA to a chromosome, and efficient incorporation of the desired nucleic acid into the chromosome can be achieved. In such transfers of Tol2 transposons into chromosomes, DNAs other than the transposon DNA, such as unnecessary DNAs like vector sequences, are not transferred, even if the Tol2 transposon DNA has been incorporated into a vector. Therefore, these transgenic mutation systems are expected to be useful not only for production of transgenic animals and the like, but also as safe systems for gene therapy. That is, they may also be utilized medically as systems for supplementing disease-causing genes and the like.

[Methods for Producing Mutant Mammalian Cells]

Further, the present invention relates to methods for producing mutant mammalian cells using Tol2 transposon DNAs. A first method for producing mutant mammalian cells using Tol2 transposon DNA is a method comprising a process of introducing mammalian cells with an autonomous Tol2 transposon DNA, as typified by SEQ ID NO: 3, or a vector comprising such.

The target cells of such methods are not particularly limited s to their species and the like, so long as they are mammalian cells. The target cells thus include cells derived from primates such as humans, and cells derived from rodents such as mice. Methods for introducing the above-mentioned transposon DNAs into such cells are not particularly restricted, and include liposome methods, electroporation methods, calcium phosphate methods, and gene gun methods. For germ cells and the like, microinjection methods and such can be used.

Introducing autonomous Tol2 transposon DNAs into target mammalian cells in this way enables transposition of Tol2 transposon DNAs into chromosomes by the action of transposases encoded by the autonomous Tol2 transposon DNAs in the cells, thus producing mutant mammalian cells.

A second method for producing mutant mammalian cells is a method comprising a step of introducing the cells of a non-human mammal with an nonautonomous Tol2 transposon DNA, such as the nucleotide sequence of SEQ ID NO: 4, or a vector comprising such, and at least one of a Tol2 transposase DNA as typified by the nucleotide sequence of SEQ ID NO: 1, a vector comprising this DNA, a transposase typified by the amino acid sequence of SEQ ID NO: 2, and a RNA encoding this transposase.

Since the above-mentioned first method may cause retransfer of Tol2 transposases in the mutant mammalian cells produced, the second method using a nonautonomous Tol2 transposon is preferred for reducing the possibility of retransfer. Also in the second production method, the target mammalian cells are not as restricted as in the above-mentioned first production method.

In the methods for introducing a Tol2 transposon DNA along with a source for supplying a transposase to target cells, such as a Tol2 transposase DNA, a vector comprising this DNA or a Tol2 transposase RNA, co-transfection may be performed using the various methods described for the first production method (e.g., liposome methods, electroporation methods, calcium phosphate methods, gene gun methods, and microinjection methods). When a Tol2 transposase DNA is used as a transposase supply source, it can be subjected to the above-mentioned co-transfection in a fragment or vector separate from that of the nonautonomous Tol2 transposon DNA. Alternatively, both DNAs can be incorporated into the same vector for introduction to mammalian cells by any of the above-mentioned methods. When a Tol2 transposase protein is directly used as a Tol2 transposase supply source, the protein may be supplied simultaneously in transfecting the above-mentioned nonautonomous Tol2 transposon DNA into target cells by microinjection, or it may be supplied by endocytosis.

The above-mentioned methods for producing mutant mammalian cells can mainly be utilized as methods capable of transferring Tol2 transposons into chromosomes to produce cells in which a gene or the like is randomly knocked out. The cells thus produced can be used as tools for forward genetics. That is, the phenotype of the cells may change due to the destruction of some gene. Therefore, by analyzing the phenotypes of cells produced by such methods, and identifying gene loci into which transposon DNAs have been inserted in cells that comprise altered phenotypes, it is possible to screen for functional genes. The analysis of phenotypes includes not only analysis of expression on the surface of cells but also analysis of wide kinetic change in cells. Identification of a locus into which a transposon DNA has been inserted can be performed by, for example, hybridization using the transposon DNA used for introducing the mutation, or its portion, as a probe.

The methods for producing mutant mammalian cells of the present invention can be used not only as methods for producing random knockout mammalian cells as described above, but also for producing transgenic cells into which a nucleic acid such as a desired gene has been introduced. When producing such cells into which a desired exogenous gene or the like has been introduced, a desired nucleic acid such as a gene whose function is to be analyzed is pre-inserted into an above-mentioned nonautonomous Tol2 transposon DNA, or a nonautonomous transposon DNA region on a vector comprising the same. Such nonautonomous Tol2 transposon DNA or vector comprising the same, into which a desired nucleic acid has been inserted, is then introduced into target mammalian cells. An above-mentioned Tol2 transposase supply source (Tol2 transposase DNAs, vectors comprising these DNAs, Tol2 transposase RNAs, or Tol2 transposase proteins) is simultaneously provided to the cells along with the introduction of a nonautonomous Tol2 transposon DNA, or are provided at different times. By the action of this Tol2 transposase, the Tol2 transposon DNA comprising the desired nucleic acid transfers to a chromosome in the cells, and the desired nucleic acid is efficiently inserted into the chromosome. Thus, by using a transposon of the present invention as a carrier for transporting a desired gene to a chromosome, desired nucleic acids, such as genes and DNAs whose functions are to be investigated, can be efficiently inserted into chromosomes. Cells produced here can be used as material for reverse genetics. That is, if introducing a cell chromosome with a transposon DNA and a desired nucleic acid causes a change in cell phenotype, the function of this desired nucleic acid can be analyzed by analyzing this phenotype.

[Methods for Producing Genetically Modified Animals]

Another embodiment of the present invention relates to methods for producing genetically modified animals using Tol2 transposons.

A first method for producing genetically modified animals is a method comprising a step of injecting a non-human mammal with an autonomous Tol2 transposon DNA, typified by the nucleotide sequence of SEQ ID NO: 3, or a vector comprising the same.

The target mammals of these methods include primates such as monkeys, and rodents such as mice, so long as they are non-human mammals. As methods for introducing these mammals with the above-mentioned transposon DNAs or vectors, transport into an animal body can be by injection that is intravascular, intramuscular, subcutaneous, or the like. For example, in the case of a mouse, its tail is cut and the above-mentioned DNA or the like can be injected through a tail vein. Thus, DNAs injected in this way are distributed into a mammal's tissues and the like, and reach the somatic cells, reproductive cells, and so on. The Tol2 transposon DNA transfers to a chromosome in any of these cells, and a mammal comprising a chromosomal mutation can thus be produced. When the above-mentioned transposon DNA transfers to a chromosome in a reproductive cell, this transposon DNA can be transferred from the generated mammal to its descendents, producing many mutant mammals.

A second method is a method comprising a step of introducing a non-human mammal with a nonautonomous Tol2 transposon DNA, such as a nucleotide sequence of SEQ ID NO: 3 or a vector comprising the same, and at least one of a Tol2 transposase DNA typified by the nucleotide sequence of SEQ ID NO: 1, a vector comprising this DNA, a Tol2 transposase typified by the amino acid sequence of SEQ ID NO: 2, and a Tol2 transposase RNA encoding the same.

The target animals for this second method are also non-human mammals. Injection of mammals with these nonautonomous Tol2 transposon DNAs or the like, and a transposase supply source (Tol2 transposase DNAs, vectors comprising such DNAs, Tol2 transposases, or Tol2 transposase RNAs) can be performed by intravascular injection or the like, as in the first method above. Nonautonomous Tol2 transposon DNAs or vectors may be injected simultaneously with the above-mentioned transposase supply sources, or one may be injected prior to the other.

Thus, by injecting mammalian cells with transposase supply sources and nonautonomous Tol2 transposon DNAs or the like, these injected materials are distributed to the mammal's tissues and the like, and reach somatic cells, reproductive cells, and so on. The transposases act on the nonautonomous Tol2 transposon DNAs in such cells, transferring the nonautonomous Tol2 transposon DNA to a chromosome and producing mammals that comprise chromosomal mutations. Note that in such cases, when the above-mentioned transposon DNAs transfer to chromosomes in reproductive cells, the transposon DNAs can be transferred from the generated mammal to its descendents, and many mutant mammals can be produced.

A third method is a variation of the second method, comprising a step of generating individuals by mating a nonhuman mammal comprising a Tol2 transposase DNA as typified by the nucleotide sequence of SEQ ID NO: 1, with a nonhuman mammal comprising a nonautonomous Tol2 transposon DNA, such as the nucleotide sequence of SEQ ID NO: 4. Thus, this method is different from the second method of injecting a Tol2 transposase supply source and a nonautonomous Tol2 transposon DNA into one mammal, in that a mammal previously comprising a nonautonomous Tol2 transposon DNA and a mammal comprising a transposase DNA are mated to transfer both DNAs into offspring. Thus, to transfer these DNAs to offspring, the nonautonomous Tol2 transposon DNAs and Tol2 transposase DNAs must be maintained in the reproductive cells of the respective mammals. In addition, since mating is prerequisite to this method, both mammals must be of different sex.

Parent mammals comprising an autonomous Tol2 transposon DNA may be produced by the above-mentioned second method; or generated from germ cells or the like comprising autonomous Tol2 transposon DNAs; or produced without the action of a Tol2 transposase by usual methods for producing transgenic individuals, that integrate DNAs into chromosomes. The other parent mammals, comprising Tol2 transposase DNAs, can be produced by usual methods for producing transgenic individuals ("Manipulating the mouse embryo, a laboratory manual", second edition, Kindai Syuppan, Brigid Hogan et al., translated by Kazuya Yamauchi et al.).

The above three methods for producing genetically modified mammals can be used mainly for the purpose of producing knockout individuals in which a mutation has been introduced into a chromosome. Accordingly, mammalian cells produced by these methods can be used to screen novel functional genes. That is, the phenotypes of mutant mammals produced herein are analyzed, and animals comprising mutant phenotypes are selected. These phenotypes may be systemic, or specific to certain organs or tissues. Functional genes may also be screened by identifying the tissue, chromosomal position, and such, in which transposon DNA is present in animals thus selected.

The methods for producing genetically modified animals of the present invention can be utilized not only as methods for producing random gene knockout animals, as described above, but also as methods for producing transgenic animals into which desired nucleic acids have been introduced. When carrying out the methods of the present invention for such purposes, a desired nucleic acid is pre-inserted into an above-described nonautonomous Tol2 transposon DNA, or a nonautonomous transposon DNA region on a vector. The above-mentioned second production method of the present invention is then performed using a nonautonomous transposon DNA into which the desired nucleic acid has been inserted, or a vector comprising the same. That is, a nonautonomous Tol2 transposon DNA into which a desired nucleic acid has been inserted, or the vector comprising this, is injected into a mammal. In this injection, to transfer a nonautonomous Tol2 transposon, a source of a Tol2 transposase (Tol2 transposase DNAs, vectors comprising these, Tol2 transposase RNAs, or Tol2 transposase proteins) is injected simultaneously or separately into the mammal. In this mammal, the action of the transposase transfers the nonautonomous transposon DNA into a chromosome, and this transfer of nonautonomous transposon DNA produces a mutant mammal that comprises an arbitrary nucleic acid introduced into a chromosome. According to the present methods, a desired nucleic acid can be efficiently introduced into a mammal using the function of a transposon. In addition, by using these methods, a desired nucleic acid can be efficiently introduced into a mammal to impart a desired function. Furthermore, these methods can also be used as methods for analyzing the function of a gene, by placing a desired nucleic acid, such as a test nucleic acid whose function is to be analyzed, on to a transposon and producing mutant mammals by a present method, and analyzing the phenotype of the produced animals.

BRIEF DESCRIPTION OF THE DRAWINGS

FIG. 2 shows the results of analyzing genomic DNA extracted from G418 resistant ES cell clones transformed using pT2KPKneo and pCAGGS-T2TP (clones #1 to #10), and from G418 resistant ES cell clones transformed using pT2KPKneo and pCAGGS (clones #11 to #20). (a) photographs showing the results of Southern blot analysis of genomic DNA after digestion with Bg1II using the probe shown in FIG. 1. (b) photographs showing the results of PCR analysis using the f20 and ex4f primers (upper panel), and the PGKr1 and r7 primers (lower panel). PCR using the PGKr1 and r7 primers was performed to confirm the presence of Tol2 DNA in the DNA samples. In the drawing, M represents a marker, E represents non-transformed ES cell DNA, P represents pT2KPKneo plasmid DNA, and "-" represents a blank (no DNA). (c) a diagram showing the DNA sequences at integration sites of clones 1, 9, and 10 (SEQ ID NOS: 8-10). In these sequences, the Tol2 sequences are italicized, and the eight base forward repeating sequences are underlined.

BEST MODE FOR CARRYING OUT THE INVENTION

Figure 1:
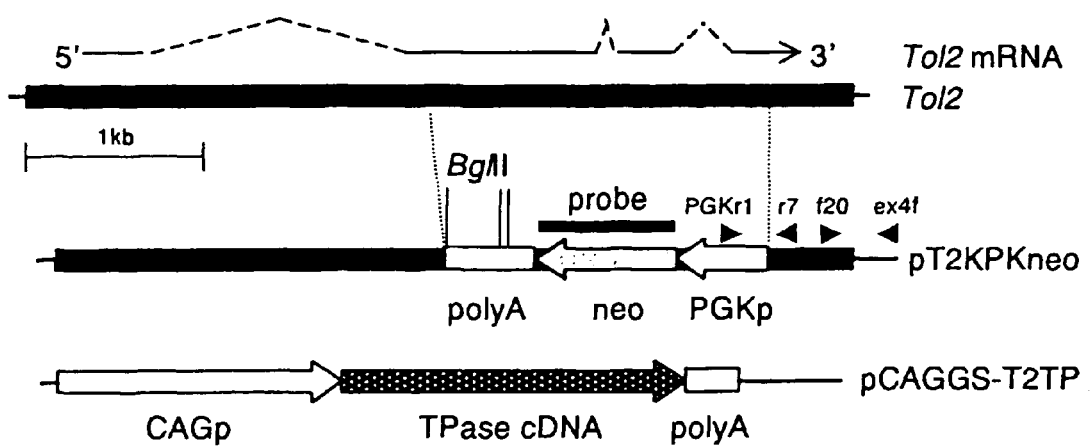
FIG. 1 is a schematic diagram showing the structure of Tol2, pT2 KPKneo, and a transposase expression vector. A Tol2 transposase mRNA is transcribed from a transposase DNA comprising three of the introns on the Tol2 transposon. pT2 KPKneo has a structure whereby a part of Tol2 is substituted with a PGK-neo cassette (the dotted lines), and has three BglII recognition sites. pCAGGS-T2 TP is constructed by cloning Tol2 cDNA into pCAGGS (Niwa, H., Yamamura, K. & Miyazaki, J. Gene 108, 193-200 (1991)). The black line and black arrowheads above pT2 KPKneo respectively show the probe and primers used in this analysis.

The present invention will be explained in more detail with reference to an Example, but is not to be construed as being limited thereto.

EXAMPLE 1

Analysis of Transposition of Tol2 in Mammal

To develop novel transposons that can be used in mammals, Tol2's ability to transpose in mammalian cells was analyzed using the following 2-component analysis system:

Two plasmids were used in the 2-component analysis system: pT2 KPKneo provided with a cis element of Tol2, and pCAGGS-T2TP provided with a trans element of Tol2 (FIG. 1). First, plasmid pT2 KPKneo was constructed as follows: pTol2-tyr (Kawakami, K., Shima, A., & Kawakami, N. Proc. Natl. Acad. Sci. USA 97, 11403-11408. (2000)) was modified to construct a nonautonomous transposon DNA (SEQ ID NO: 4) by connecting the region from 1 to 2229 and the region from 4147 to 4682 of the full-length sequence of Tol2 (SEQ ID NO: 3), through a linker sequence comprising a XhoI recognition sequence. This DNA was incorporated into the pCAGGS plasmid (Niwa, H., Yamamura, K. & Miyazaki, J. Gene 108, 193-200 (1991)) to construct a nonautonomous Tol2 transposon vector. To introduce a drug-resistant marker into the above vector, a PGK-neo cassette (a cassette comprising a neomycin-resistant gene connected downstream of a PGK promoter, and PGK polyadenylation signal sequence further downstream of this) was inserted into XhoI in the above-mentioned nonautonomous transposon DNA. pT2 KPKneo was thus constructed. Another plasmid pCAGGS-T2TP was constructed by incorporating Tol2 cDNA (SEQ ID NO: 1) into pCAGGS.

The above-mentioned pT2 KPKneo (50 µg) was introduced into mouse ES cells by electroporation, together with pCAGGS-T2TP (300 µg) or pCAGGS vector carrying no transposase (300 µg). After electroporation, cells were plated on several dishes, and cultured using a standard ES cell culturing method in the presence of G418 (175 µg/ml). In the co-transfection of pT2 KPKneo and pCAGGS-T2TP, a total number of about $1.1 \times 10^4$ G418-resistant (G418$^R$) colonies were obtained. On the other hand, in the co-transfection of pT2 KPKneo and pCAGGS vector, about fifty G418$^R$ colonies were obtained. That is, the transformation efficiency when co-transfecting with pCAGGS-T2TP was about 200 times that when using pCAGGS vector. This result showed that the transposase expressed from pCAGGS-T2TP exerts a positive effect on transformation efficiency.

To analyze whether or not this high efficiency transformation occurred because of chromosomal integration by the transposition of the transfer cassette, ten G418-resistant colonies obtained in each of the above transfection experiments were isolated and cultured, genomic DNA was extracted from each colony, and various analyses were performed. Southern blot analysis of the genomic DNA showed that the above-mentioned transfer cassette was inserted into a chromosome in these G418-resistant ES cell colonies (FIG. 2a). The chromosomally inserted sequence was then analyzed by PCR using primers f20 (5'-TTTACTCAAGTAAGATTCTAG-3' (SEQ ID NO: 0.5)) and ex4f (5'-GCTACTACATGGTGC-CATTCCT-3' (SEQ ID NO: 6)), as shown in FIG. 1. From ES colonies obtained by co-transfection using pCAGGS-T2TP (FIG. 2b, upper panel, lanes 1 to 10), an amplified DNA band was not detected. On the other hand, from ES colonies obtained by co-transfection using pCAGGS (FIG. 2b, upper panel, lanes 11 to 20), about 200 bp DNA band was amplified. The results of this PCR showed that, in the ES clones co-transfected with pCAGGS-T2TP, only the transfer cassette was inserted into the ES clone, and an adjacent vector sequence was not inserted.

Finally, to analyze DNA fragments comprising connecting portions of the inserted Tol2 sequence and adjacent mouse genomic sequences, inverse PCR was conducted on three ES clones co-transfected with pCAGGS-T2TP. The amplified fragments were cloned and sequenced. The three ES clones used here are clones in which insertion of a single Tol2 sequence was detected using Southern blotting (FIG. 2a, lanes 1, 9, and 10). In each of these three clones, the Tol2 insert was surrounded by mouse chromosomal DNA and an 8 bp forward repeat sequence. This sequence was always discovered and formed in Tol2 target sites (FIG. 2c). Wild type DNA from the above region prior to transfer of Tol2 was cloned from untransfected ES cells. Each region comprised one copy of the 8 bp sequence. These results showed that the transposase produced by pCAGGS-T2TP functioned in mouse ES cells, and by the action of this transposase, a nonautonomous Tol2 element was transferred and inserted into a chromosome. In clone #10, a partial genomic sequence comprising the Tol2 insert region coincided completely with a mouse EST sequence (BB629503) (118 bp/118 bp), and the end of this homology terminated at GT on the chromosome sequence. This suggests the transfer and insertion of Tol2 into an exon in this clone.

Tol2 was shown to be able to transfer not only in fish but also in mice, which are mammals. Although host factors correlated with the Tol2 transposition reaction are not known, such factors may be commonly present in these hosts.

Tol2 belongs to the transposon hAT family, which is different from the Tc1/mariner family to which Sleeping Beauty belongs. This means that both transposon systems may have different properties such as transfer efficiency, preferred transfer sequences, and the like. In fact, although Sleeping Beauty usually transfers to TA sequences (Ivics, Z., Hackett, P. B., Plasterk, R. H., & Izsvak, Z. Cell 91, 501-510 (1997)), such specificity was not observed in Tol2 (FIG. 2C, Koga, A., Suzuki, M., Inagaki, H., Bessho, Y., & Hori, H. Nature 383, 30 (1996), Kawakami, K., Shima, A., & Kawakami, N. Proc. Natl. Acad. Sci. USA 97, 11403-11408 (2000), Koga, A., & Hori, H. Genetics 156, 1243-1247 (2000)). Therefore, Tol2 can be used as a novel tool for methods of producing transgenic mammals and methods of introducing mutations.

INDUSTRIAL APPLICABILITY

The present invention provides novel transposons that function in mammals. Such transposons can be utilized as autonomous transposons comprising a transposase, or non-autonomous transposons with a separate transposase. Such transposons can be powerful tools in producing knockout animals and transgenic animals. The present invention also provides methods for modifying mammals using these transposons and the like. These methods are expected to be significantly useful in analyzing the function of various mammalian genes, and in discovering functional genes.

The invention claimed is:

1. A mammalian host cell comprising a DNA or a vector comprising the DNA, wherein the DNA comprises the nucleotide sequence of SEQ ID NO: 3.

2. A mammalian host cell comprising a nonautonomous transposon DNA or a vector comprising a nonautonomous transposon DNA, wherein said nonautonomous transposon DNA comprises a nucleotide sequence of SEQ ID NO:3, wherein said nucleotide sequence contains a deletion mutation, an insertion mutation, or a substitution mutation in a transposase-coding region of SEQ ID NO: 3.

3. A method for producing genetically modified mammalian cells, comprising the step of introducing a DNA comprising the nucleotide sequence of SEQ ID NO: 3 or a vector comprising the DNA into mammalian cells.

4. A method for producing genetically modified mammals, comprising the step of injecting a DNA comprising the nucleotide sequence of SEQ ID NO: 3 or a vector comprising the DNA into nonhuman mammals.

5. The mammalian cell of claim 2, wherein the deletion mutation in the transposase-coding region is at positions 2230 to 4146 in SEQ ID NO: 3.

6. A method for producing genetically modified mammalian cells, comprising introducing a DNA comprising the nucleotide sequence of SEQ ID NO: 3 or a vector comprising the DNA into mammalian cells, and selecting a cell in which the DNA is inserted into a chromosome.

7. A method for producing genetically modified mammals, comprising injecting a DNA comprising the nucleotide sequence of SEQ ID NO: 3 or a vector comprising the DNA into nonhuman mammals, and selecting a nonhuman mammal in which the DNA is inserted into a chromosome.

8. The mammalian cells of claim 1, wherein the mammalian cells are mouse cells.

9. The mammalian cells of claim 2, wherein the mammalian cells are mouse cells.

10. The method of claim 3, wherein the mammalian cells are mouse cells.

11. The method of claim 6, wherein the mammalian cells are mouse cells.

12. The method of claim 4, wherein the mammal is a mouse.

13. The method of claim 7, wherein the mammal is a mouse.

* * * * *

SEQUENCE LISTING

<160> NUMBER OF SEQ ID NOS: 10

<210> SEQ ID NO 1
<211> LENGTH: 2156
<212> TYPE: DNA
<213> ORGANISM: Oryzias latipes

<400> SEQUENCE: 1

```
acgtcatgtc acatctatta ccacaatgca cagcaccttg acctggaaat tagggaaatt      60
ataacagtca atcagtggaa gaaaatggag gaagtatgtg attcatcagc agctgcgagc     120
agcacagtcc aaaatcagcc acaggatcaa gagcacccgt ggccgtatct tcgcgaattc     180
ttttctttaa gtggtgtaaa taaagattca ttcaagatga aatgtgtcct ctgtctcccg     240
cttaataaag aaatatcggc cttcaaaagt tcgccatcaa acctaaggaa gcatattgag     300
agaatgcacc caaattacct caaaaactac tctaaattga cagcacagaa gagaaagatc     360
gggacctcca cccatgcttc cagcagtaag caactgaaag ttgactcagt tttcccagtc     420
aaacatgtgt ctccagtcac tgtgaacaaa gctatattaa ggtacatcat tcaaggactt     480
```

-continued

```
catcctttca gcactgttga tctgccatca tttaaagagc tgattagtac actgcagcct    540
ggcatttctg tcattacaag gcctacttta cgctccaaga tagctgaagc tgctctgatc    600
atgaaacaga aagtgactgc tgccatgagt gaagttgaat ggattgcaac acaacggat    660
tgttggactg cacgtagaaa gtcattcatt ggtgtaactg ctcactggat caaccctgga    720
agtcttgaaa gacattccgc tgcacttgcc tgcaaaagta taatgggctc tcatactttt    780
gaggtactgg ccagtgccat gaatgatatc cactcagagt atgaaatacg tgacaaggtt    840
gtttgcacaa ccacagacag tggttccaac tttatgaagg cttttcagagt ttttggtgtg    900
gaaaacaatg atatcgagac tgaggcaaga aggtgtgaaa gtgatgacac tgattctgaa    960
ggctgtggtg agggaagtga tggtgtggaa ttccaagatg cctcacgagt cctggaccaa   1020
gacgatggct tcgaattcca gctaccaaaa catcaaaagt gtgcctgtca cttacttaac   1080
ctagtctcaa gcgttgatgc ccaaaaagct ctctcaaatg aacactacaa gaaactctac   1140
agatctgtct ttggcaaatg ccaagcttta tggaataaaa gcagccgatc ggctctagca   1200
gctgaagctg ttgaatcaga aagccggctt cagctttaa ggccaaacca acgcggtgg    1260
aattcaactt ttatggctgt tgacagaatt cttcaaattt gcaagaagc aggagaaggc    1320
gcacttcgga atatatgcac ctctcttgag gttccaatgt ttaatccagc agaaatgctg    1380
ttcttgacag agtgggccaa cacaatgcgt ccagttgcaa aagtactcga catcttgcaa    1440
gcggaaacga atacacagct ggggtggctg ctgcctagtg tccatcagtt aagcttgaaa    1500
cttcagcgac tccaccattc tctcaggtac tgtgacccac ttgtggatgc cctacaacaa    1560
ggaatccaaa cacgattcaa gcatatgttt gaagatcctg agatcatagc agctgccatc    1620
cttctcccta aatttcggac tcttggaca aatgatgaaa ccatcataaa acgaggcatg    1680
gactacatca gagtgcatct ggagcctttg gaccacaaga aggaattggc caacagttca    1740
tctgatgatg aagatttttt cgcttctttg aaaccgacaa cacatgaagc cagcaaagag    1800
ttggatggat atctggcctg tgtttcagac accagggagt ctctgctcac gtttcctgct    1860
atttgcagcc tctctatcaa gactaataca cctcttcccg catcggctgc ctgtgagagg    1920
cttttcagca ctgcaggatt gcttttcagc cccaaaagag ctaggcttga cactaacaat    1980
tttgagaatc agcttctact gaagttaaat ctgaggtttt acaactttga gtagcgtgta    2040
ctggcattag attgtctgtc ttatagtttg ataattaaat acaaacagtt ctaaagcagg    2100
ataaaacctt gtatgcattt catttaatgt tttttgagat taaaagctta aacaag        2156
```

<210> SEQ ID NO 2
<211> LENGTH: 649
<212> TYPE: PRT
<213> ORGANISM: Oryzias latipes

<400> SEQUENCE: 2

Met Glu Glu Val Cys Asp Ser Ser Ala Ala Ser Ser Thr Val Gln
1               5                   10                  15

Asn Gln Pro Gln Asp Gln Glu His Pro Trp Pro Tyr Leu Arg Glu Phe
            20                  25                  30

Phe Ser Leu Ser Gly Val Asn Lys Asp Ser Phe Lys Met Lys Cys Val
        35                  40                  45

Leu Cys Leu Pro Leu Asn Lys Glu Ile Ser Ala Phe Lys Ser Ser Pro
    50                  55                  60

Ser Asn Leu Arg Lys His Ile Glu Arg Met His Pro Asn Tyr Leu Lys
65                  70                  75                  80

-continued

```
Asn Tyr Ser Lys Leu Thr Ala Gln Lys Arg Lys Ile Gly Thr Ser Thr
                85                  90                  95

His Ala Ser Ser Lys Gln Leu Lys Val Asp Ser Val Phe Pro Val
            100                 105                 110

Lys His Val Ser Pro Val Thr Val Asn Lys Ala Ile Leu Arg Tyr Ile
            115                 120                 125

Ile Gln Gly Leu His Pro Phe Ser Thr Val Asp Leu Pro Ser Phe Lys
        130                 135                 140

Glu Leu Ile Ser Thr Leu Gln Pro Gly Ile Ser Val Ile Thr Arg Pro
145                 150                 155                 160

Thr Leu Arg Ser Lys Ile Ala Glu Ala Ala Leu Ile Met Lys Gln Lys
                165                 170                 175

Val Thr Ala Ala Met Ser Glu Val Glu Trp Ile Ala Thr Thr Thr Asp
            180                 185                 190

Cys Trp Thr Ala Arg Arg Lys Ser Phe Ile Gly Val Thr Ala His Trp
            195                 200                 205

Ile Asn Pro Gly Ser Leu Glu Arg His Ser Ala Ala Leu Ala Cys Lys
        210                 215                 220

Arg Leu Met Gly Ser His Thr Phe Glu Val Leu Ala Ser Ala Met Asn
225                 230                 235                 240

Asp Ile His Ser Glu Tyr Glu Ile Arg Asp Lys Val Val Cys Thr Thr
                245                 250                 255

Thr Asp Ser Gly Ser Asn Phe Met Lys Ala Phe Arg Val Phe Gly Val
            260                 265                 270

Glu Asn Asn Asp Ile Glu Thr Glu Ala Arg Arg Cys Glu Ser Asp Asp
        275                 280                 285

Thr Asp Ser Glu Gly Cys Gly Glu Gly Ser Asp Gly Val Glu Phe Gln
        290                 295                 300

Asp Ala Ser Arg Val Leu Asp Gln Asp Gly Phe Glu Phe Gln Leu
305                 310                 315                 320

Pro Lys His Gln Lys Cys Ala Cys His Leu Leu Asn Leu Val Ser Ser
                325                 330                 335

Val Asp Ala Gln Lys Ala Leu Ser Asn Glu His Tyr Lys Lys Leu Tyr
            340                 345                 350

Arg Ser Val Phe Gly Lys Cys Gln Ala Leu Trp Asn Lys Ser Ser Arg
            355                 360                 365

Ser Ala Leu Ala Ala Glu Ala Val Glu Ser Glu Ser Arg Leu Gln Leu
        370                 375                 380

Leu Arg Pro Asn Gln Thr Arg Trp Asn Ser Thr Phe Met Ala Val Asp
385                 390                 395                 400

Arg Ile Leu Gln Ile Cys Lys Glu Ala Gly Glu Gly Ala Leu Arg Asn
                405                 410                 415

Ile Cys Thr Ser Leu Glu Val Pro Met Phe Asn Pro Ala Glu Met Leu
            420                 425                 430

Phe Leu Thr Glu Trp Ala Asn Thr Met Arg Pro Val Ala Lys Val Leu
        435                 440                 445

Asp Ile Leu Gln Ala Glu Thr Asn Thr Gln Leu Gly Trp Leu Leu Pro
        450                 455                 460

Ser Val His Gln Leu Ser Leu Lys Leu Gln Arg Leu His His Ser Leu
465                 470                 475                 480

Arg Tyr Cys Asp Pro Leu Val Asp Ala Leu Gln Gln Gly Ile Gln Thr
            485                 490                 495
```

```
Arg Phe Lys His Met Phe Glu Asp Pro Glu Ile Ile Ala Ala Ala Ile
            500                 505                 510
Leu Leu Pro Lys Phe Arg Thr Ser Trp Thr Asn Asp Glu Thr Ile Ile
            515                 520                 525
Lys Arg Gly Met Asp Tyr Ile Arg Val His Leu Glu Pro Leu Asp His
            530                 535                 540
Lys Lys Glu Leu Ala Asn Ser Ser Asp Asp Glu Asp Phe Phe Ala
545                 550                 555                 560
Ser Leu Lys Pro Thr Thr His Glu Ala Ser Lys Glu Leu Asp Gly Tyr
            565                 570                 575
Leu Ala Cys Val Ser Asp Thr Arg Glu Ser Leu Leu Thr Phe Pro Ala
            580                 585                 590
Ile Cys Ser Leu Ser Ile Lys Thr Asn Thr Pro Leu Pro Ala Ser Ala
            595                 600                 605
Ala Cys Glu Arg Leu Phe Ser Thr Ala Gly Leu Leu Phe Ser Pro Lys
            610                 615                 620
Arg Ala Arg Leu Asp Thr Asn Asn Phe Glu Asn Gln Leu Leu Leu Lys
625                 630                 635                 640
Leu Asn Leu Arg Phe Tyr Asn Phe Glu
            645

<210> SEQ ID NO 3
<211> LENGTH: 4682
<212> TYPE: DNA
<213> ORGANISM: Oryzias latipes

<400> SEQUENCE: 3
cagaggtgta aagtacttga gtaattttac ttgattactg tacttaagta ttattttttgg   60 ggatttttac tttacttgag tacaattaaa aatcaatact tttactttta cttaattaca   120 ttttttttaga aaaaaagta ctttttactc cttacaattt tatttacagt caaaaagtac   180 ttatttttttg gagatcactt cattctattt tcccttgcta ttaccaaacc aattgaattg   240
cgctgatgcc cagtttaatt taatgttat ttattctgcc tatgaaaatc gttttcacat    300
tatatgaaat tggtcagaca tgttcattgg tcctttggaa gtgacgtcat gtcacatcta   360
ttaccacaat gcacagcacc ttgacctgga aattagggaa attataacag tcaatcagtg   420
gaagaaaatg gaggaagtat gtgattcatc agcagctgcg agcagcacag tccaaaatca   480
gccacaggat caagagcacc cgtggccgta tcttcgcgaa ttcttttctt taagtggtgt   540
aaataaagat tcattcaaga tgaaatgtgt cctctgtctc ccgcttaata aagaaatatc   600
ggccttcaaa agttcgccat caaacctaag gaagcatatt gaggtaagta cattaagtat   660 tttgtttac tgatagtttt ttttttttt tttttttttt tttttgggtg tgcatgtttt    720
gacgttgatg gcgcgccttt tatatgtgta gtaggcctat tttcactaat gcatgcgatt   780
gacaatataa ggctcacgta ataaaatgct aaaatgcatt gtaattggt aacgttaggt    840 ccacgggaaa tttggcgcct attgcagctt tgaataatca ttatcattcc gtgctctcat   900
tgtgtttgaa ttcatgcaaa acacaagaaa accaagcgag aaatttttt ccaaacatgt    960 tgtattgtca aaacggtaac actttacaat gaggttgatt agttcatgta ttaactaaca  1020
ttaaataacc atgagcaata catttgttac tgtatctgtt aatctttgtt aacgttagtt  1080
aatagaaata cagatgttca ttgtttgttc atgttagttc acagtgcatt aactaatgtt  1140
aacaagatat aaagtattag taatgttga aattaacatg tatacgtgca gttcattatt   1200
agttcatgtt aactaatgta gttaactaac gaaccttatt gtaaaagtgt taccatcaaa  1260
```

```
actaatgtaa tgaaatcaat tcaccctgtc atgtcagcct tacagtcctg tgttttgtc    1320
aatataatca gaaataaaat taatgtttga ttgtcactaa atgctactgt atttctaaaa   1380
tcaacaagta tttaacatta taaagtgtgc aattggctgc aaatgtcagt tttattaaag   1440
ggttagttca cccaaaaatg aaaataatgt cattaatgac tcgccctcat gtcgttccaa   1500
gcccgtaaga cctccgttca tcttcagaac acagtttaag atattttaga tttagtccga   1560
gagctttctg tgcctccatt gagaatgtat gtacggtata ctgtccatgt ccagaaaggt   1620
aataaaaaca tcaaagtagt ccatgtgaca tcagtgggtt agttagaatt ttttgaagca   1680
tcgaatacat tttggtccaa aaataacaaa acctacgact ttattcggca ttgtattctc   1740
ttccgggtct gttgtcaatc cgcgttcacg acttcgcagt gacgctacaa tgctgaataa   1800
agtcgtaggt tttgttattt ttggaccaaa atgtattttc gatgcttcaa ataattctac   1860
ctaacccact gatgtcacat ggactacttt gatgttttta ttacctttct ggacatggac   1920
agtataccgt acatacattt tcagtggagg gacagaaagc tctcggacta aatctaaaat   1980
atcttaaact gtgttccgaa gatgaacgga ggtgttacgg gcttggaacg acatgagggt   2040
gagtcattaa tgacatcttt tcattttttgg gtgaactaac cctttaatgc tgtaatcaga   2100
gagtgtatgt gtaattgtta catttattgc atacaatata aatatttatt tgttgttttt   2160
acagagaatg cacccaaatt acctcaaaaa ctactctaaa ttgacagcac agaagagaaa   2220
gatcgggacc tccacccatg cttccagcag taagcaactg aaagttgact cagttttccc   2280
agtcaaacat gtgtctccag tcactgtgaa caaagctata ttaaggtaca tcattcaagg   2340
acttcatcct ttcagcactg ttgatctgcc atcatttaaa gagctgatta gtacactgca   2400
gcctggcatt tctgtcatta caaggcctac tttacgctcc aagatagctg aagctgctct   2460
gatcatgaaa cagaaagtga ctgctgccat gagtgaagtt gaatggattg caaccacaac   2520
ggattgttgg actgcacgta gaaagtcatt cattggtgta actgctcact ggatcaaccc   2580
tggaagtctt gaaagacatt ccgctgcact tgcctgcaaa agattaatgg gctctcatac   2640
ttttgaggta ctggccagtg ccatgaatga tatccactca gagtatgaaa tacgtgacaa   2700
ggttgtttgc acaaccacag acagtggttc caactttatg aaggctttca gagttttttgg  2760
tgtgaaaaac aatgatatcg agactgaggc aagaaggtgt gaaagtgatg acactgattc   2820
tgaaggctgt ggtgagggaa gtgatggtgt ggaattccaa gatgcctcac gagtcctgga   2880
ccaagacgat ggcttcgaat ccagctacc aaaacatcaa aagtgtgcct gtcacttact    2940
taacctagtc tcaagcgttg atgcccaaaa agctctctca aatgaacact acaagaaact   3000
ctacagatct gtctttggca aatgccaagc tttatggaat aaaagcagcc gatcggctct   3060
agcagctgaa gctgttgaat cagaaagccg gcttcagctt taaggccaa accaaacgcg    3120
gtggaattca acttttatgg ctgttgacag aattcttcaa atttgcaaag aagcaggaga   3180
aggcgcactt cggaatatat gcacctctct tgaggttcca atgtaagtgt ttttcccctc   3240
tatcgatgta aacaaatgtg ggttgttttt gtttaatact cttgtgattat gctgatttct  3300
cctgtaggtt taatccagca gaaatgctgt tcttgacaga gtgggccaac acaatgcgtc   3360
cagttgcaaa agtactcgac atcttgcaag cggaaacgaa tacacagctg ggtggctgc    3420
tgcctagtgt ccatcagtta agcttgaaac ttcagcgact ccaccattct ctcaggtact   3480
gtgacccact tgtggatgcc ctacaacaag gaatccaaac acgattcaag catatgtttg   3540
aagatcctga gatcatagca gctgccatcc ttctccctaa atttcggacc tcttggacaa   3600
```

-continued

```
atgatgaaac catcataaaa cgaggtaaat gaatgcaagc aacatacact tgacgaattc      3660
taatctgggc aacctttgag ccataccaaa attattcttt tatttattta ttttttgcact    3720 ttttaggaat gttatatccc atctttggct gtgatctcaa tatgaatatt gatgtaaagt      3780
attcttgcag caggttgtag ttatccctca gtgtttcttg aaaccaaact catatgtatc      3840
atatgtggtt tggaaatgca gttagatttt atgctaaaat aagggatttg catgatttta      3900
gatgtagatg actgcacgta aatgtagtta atgacaaaat ccataaaatt tgttcccagt      3960
cagaagcccc tcaaccaaac ttttctttgt gtctgctcac tgtgcttgta ggcatggact      4020
acatcagagt gcatctggag cctttggacc acaagaagga attggccaac agttcatctg      4080
atgatgaaga ttttttcgct tctttgaaac cgacaacaca tgaagccagc aaagagttgg      4140
atggatatct ggcctgtgtt tcagacacca gggagtctct gctcacgttt cctgctattt      4200
gcagcctctc tatcaagact aatacacctc ttcccgcatc ggctgcctgt gagaggcttt      4260
tcagcactgc aggattgctt ttcagcccca aaagagctag gcttgacact aacaattttg      4320
agaatcagct tctactgaag ttaaatctga ggttttacaa ctttgagtag cgtgtactgg      4380
cattagattg tctgtcttat agtttgataa ttaaatacaa acagttctaa agcaggataa      4440
aaccttgtat gcatttcatt taatgttttt tgagattaaa agcttaaaca agaatctcta      4500
gttttctttc ttgcttttac ttttacttcc ttaatactca agtacaattt taatggagta      4560
cttttttact tttactcaag taagattcta gccagatact tttactttta attgagtaaa      4620
attttcccta agtacttgta ctttcacttg agtaaaattt ttgagtactt tttacacctc      4680
tg                                                                    4682
```

<210> SEQ ID NO 4
<211> LENGTH: 2788
<212> TYPE: DNA
<213> ORGANISM: Artificial Sequence
<220> FEATURE:
<223> OTHER INFORMATION: Nonautonomous transposon DNA

<400> SEQUENCE: 4

```
cagaggtgta aagtacttga gtaattttac ttgattactg tacttaagta ttattttggg       60 ggattttttac tttacttgag tacaattaaa aatcaatact tttacttttta cttaattaca    120 tttttttaga aaaaaaagta cttttttactc cttacaattt tatttacagt caaaaagtac     180
ttattttttg gagatcactt cattctattt tcccttgcta ttaccaaacc aattgaattg      240
cgctgatgcc cagtttaatt taaatgttat ttattctgcc tatgaaaatc gttttcacat      300
tatatgaaat tggtcagaca tgttcattgg tcctttggaa gtgacgtcat gtcacatcta      360
ttaccacaat gcacagcacc ttgacctgga aattagggaa attataacag tcaatcagtg      420
gaagaaaatg gaggaagtat gtgattcatc agcagctgcg agcagcacag tccaaaatca      480
gccacaggat caagagcacc cgtggccgta tcttcgcgaa ttcttttctt taagtggtgt      540
aaataaagat tcattcaaga tgaaatgtgt cctctgtctc ccgcttaata agaaatatc      600 ggccttcaaa agttcgccat caaacctaag gaagcatatt gaggtaagta cattaagtat      660
tttgttttac tgatagtttt tttttttttt tttttttttt ttttgggtg tgcatgttttt     720 gacgttgatg gcgcgccttt tatatgtgta gtaggcctat tttcactaat gcatgcgatt      780
gacaatataa ggctcacgta ataaaatgct aaaatgcatt tgtaattggt aacgttaggt      840
ccacgggaaa tttggcgcct attgcagctt tgaataatca ttatcattcc gtgctctcat      900
tgtgtttgaa ttcatgcaaa acacaagaaa accaagcgag aaatttttttt ccaaacatgt    960
```

-continued

```
tgtattgtca aaacggtaac actttacaat gaggttgatt agttcatgta ttaactaaca    1020
ttaaataacc atgagcaata catttgttac tgtatctgtt aatctttgtt aacgttagtt    1080
aatagaaata cagatgttca ttgtttgttc atgttagttc acagtgcatt aactaatgtt    1140
aacaagatat aaagtattag taaatgttga aattaacatg tatacgtgca gttcattatt    1200
agttcatgtt aactaatgta gttaactaac gaaccttatt gtaaaagtgt taccatcaaa    1260
actaatgtaa tgaaatcaat tcaccctgtc atgtcagcct tacagtcctg tgtttttgtc    1320
aatataatca gaaataaaat taatgtttga ttgtcactaa atgctactgt atttctaaaa    1380
tcaacaagta tttaacatta taaagtgtgc aattggctgc aaatgtcagt tttattaaag    1440
ggttagttca cccaaaaatg aaaataatgt cattaatgac tcgccctcat gtcgttccaa    1500
gcccgtaaga cctccgttca tcttcagaac acagtttaag atattttaga tttagtccga    1560
gagctttctg tgcctccatt gagaatgtat gtacggtata ctgtccatgt ccagaaaggt    1620
aataaaaaca tcaaagtagt ccatgtgaca tcagtgggtt agttagaatt ttttgaagca    1680
tcgaatacat tttggtccaa aaataacaaa acctacgact ttattcggca ttgtattctc    1740
ttccgggtct gttgtcaatc cgcgttcacg acttcgcagt gacgctacaa tgctgaataa    1800
agtcgtaggt tttgttattt ttggaccaaa atgtattttc gatgcttcaa ataattctac    1860
ctaacccact gatgtcacat ggactacttt gatgttttta ttacctttct ggacatggac    1920
agtataccgt acatacattt tcagtggagg gacagaaagc tctcggacta aatctaaaat    1980
atcttaaact gtgttccgaa gatgaacgga ggtgttacgg gcttggaacg acatgagggt    2040
gagtcattaa tgacatcttt tcattttttgg gtgaactaac cctttaatgc tgtaatcaga    2100
gagtgtatgt gtaattgtta catttattgc atacaatata aatatttatt tgttgttttt    2160
acagagaatg cacccaaatt acctcaaaaa ctactctaaa ttgacagcac agaagagaaa    2220
gatcgggaca gatctcatat gctcgagggc ccatctggcc tgtgtttcag acaccaggga    2280
gtctctgctc acgtttcctg ctatttgcag cctctctatc aagactaata cacctcttcc    2340
cgcatcggct gcctgtgaga ggcttttcag cactgcagga ttgcttttca gccccaaaag    2400
agctaggctt gacactaaca attttgagaa tcagcttcta ctgaagttaa atctgaggtt    2460
ttacaacttt gagtagcgtg tactggcatt agattgtctg tcttatagtt tgataattaa    2520
atacaaacag ttctaaagca ggataaaacc ttgtatgcat ttcatttaat gttttttgag    2580
attaaaagct taaacaagaa tctctagttt tcttttcttgc ttttacttttt acttccttaa    2640 tactcaagta caatttaat ggagtacttt tttactttta ctcaagtaag attctagcca    2700 gatacttta cttttaattg agtaaaattt tccctaagta cttgtacttt cacttgagta    2760 aaattttga gtactttta cacctctg                                         2788
```

<210> SEQ ID NO 5
<211> LENGTH: 21
<212> TYPE: DNA
<213> ORGANISM: Artificial Sequence
<220> FEATURE:
<223> OTHER INFORMATION: Primer used to analyze the chromosomally
      inserted sequence

<400> SEQUENCE: 5
tttactcaag taagattcta g                                              21

<210> SEQ ID NO 6
<211> LENGTH: 22

```
<212> TYPE: DNA
<213> ORGANISM: Artificial Sequence
<220> FEATURE:
<223> OTHER INFORMATION: Primer used to analyze the chromosomally
      inserted sequence

<400> SEQUENCE: 6
gctactacat ggtgccattc ct                                                  22

<210> SEQ ID NO 7
<211> LENGTH: 23
<212> TYPE: DNA
<213> ORGANISM: Artificial Sequence
<220> FEATURE:
<223> OTHER INFORMATION: XhoI recognition sequence

<400> SEQUENCE: 7
agatctcata tgctcgaggg ccc                                                 23

<210> SEQ ID NO 8
<211> LENGTH: 43
<212> TYPE: DNA
<213> ORGANISM: Artificial Sequence
<220> FEATURE:
<223> OTHER INFORMATION: ES clone
<220> FEATURE:
<221> NAME/KEY: misc_feature
<222> LOCATION: (22)..(22)
<223> OTHER INFORMATION: n is the Tol2 insert

<400> SEQUENCE: 8
tgggaattat gacagtagca gnctggacag tagtagcttg att                           43

<210> SEQ ID NO 9
<211> LENGTH: 43
<212> TYPE: DNA
<213> ORGANISM: Artificial Sequence
<220> FEATURE:
<223> OTHER INFORMATION: ES clone
<220> FEATURE:
<221> NAME/KEY: misc_feature
<222> LOCATION: (22)..(22)
<223> OTHER INFORMATION: n is the Tol2 insert

<400> SEQUENCE: 9
agaaaaatct ctgccattca gnctgctgcc attccaacag tct                           43

<210> SEQ ID NO 10
<211> LENGTH: 43
<212> TYPE: DNA
<213> ORGANISM: Artificial Sequence
<220> FEATURE:
<223> OTHER INFORMATION: ES clone
<220> FEATURE:
<221> NAME/KEY: misc_feature
<222> LOCATION: (22)..(22)
<223> OTHER INFORMATION: n is the Tol2 insert

<400> SEQUENCE: 10
gcgacaggga gggctgcaca gnctggggct gcagagtggt ggg                           43
```